US012295662B2

(12) United States Patent
Azimi et al.

(10) Patent No.: US 12,295,662 B2
(45) Date of Patent: May 13, 2025

(54) AUGMENTED REALITY BASED SURGICAL NAVIGATION SYSTEM

(71) Applicant: THE JOHNS HOPKINS UNIVERSITY, Baltimore, MD (US)

(72) Inventors: Ehsan Azimi, Baltimore, MD (US); Peter Kazanzides, Lutherville-Timonium, MD (US); Judy Huang, Baltimore, MD (US); Camilo Molina, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 438 days.

(21) Appl. No.: 17/906,773

(22) PCT Filed: Mar. 18, 2021

(86) PCT No.: PCT/US2021/022887
§ 371 (c)(1),
(2) Date: Sep. 20, 2022

(87) PCT Pub. No.: WO2021/188757
PCT Pub. Date: Sep. 23, 2021

(65) Prior Publication Data
US 2023/0149084 A1 May 18, 2023

Related U.S. Application Data

(60) Provisional application No. 62/992,655, filed on Mar. 20, 2020.

(51) Int. Cl.
*A61B 34/10* (2016.01)
*A61B 34/20* (2016.01)
*A61B 90/00* (2016.01)

(52) U.S. Cl.
CPC .............. *A61B 34/10* (2016.02); *A61B 34/20* (2016.02); *A61B 90/36* (2016.02);
(Continued)

(58) Field of Classification Search
CPC ......... A61B 34/10; A61B 34/20; A61B 90/36; A61B 2034/107; A61B 2034/2055;
(Continued)

(56) References Cited

U.S. PATENT DOCUMENTS

2005/0203367 A1* 9/2005 Ahmed .................. A61B 34/20
600/407
2018/0078316 A1* 3/2018 Schaewe ................ A61B 34/20
(Continued)

FOREIGN PATENT DOCUMENTS

| JP | 2017510826 A | 4/2017 |
| WO | 2015095715 A1 | 6/2015 |

OTHER PUBLICATIONS

International Preliminary Report on Patentability in corresponding Application No. PCT/US2021/022887 mailed on Sep. 29, 2022, 6 pages.
(Continued)

*Primary Examiner* — Maurice L. McDowell, Jr.
(74) *Attorney, Agent, or Firm* — MH2 Technology Law Group LLP

(57) ABSTRACT

A computer-implemented method includes: receiving, by an augmented reality device, a medical image of a surgical site, generating, by the augmented reality device, a virtual surgical site model based on the medical image; presenting, by the augmented reality device, the virtual surgical site model; receiving, by the augmented reality device, user calibration input; aligning, by the augmented reality device, the virtual surgical site model with a real-life surgical site based on the user calibration input; and displaying, by the augmented
(Continued)

reality device and after the aligning, a virtual insertion path between an incision point and a target point to aid in inserting a tool as part of performing a surgical procedure.

20 Claims, 7 Drawing Sheets

(52) U.S. Cl.
CPC . *A61B 2034/107* (2016.02); *A61B 2034/2055* (2016.02); *A61B 2090/363* (2016.02); *A61B 2090/365* (2016.02)

(58) Field of Classification Search
CPC ........ A61B 2090/363; A61B 2090/365; A61B 2034/105; A61B 2034/2057; A61B 2090/372; A61B 2090/502; G06F 3/011; G16H 30/40; G16H 50/50; G16H 20/40
See application file for complete search history.

(56) References Cited

U.S. PATENT DOCUMENTS

| | | |
|---|---|---|
| 2018/0092698 A1 | 4/2018 | Chopra et al. |
| 2019/0216452 A1 | 7/2019 | Nawana et al. |
| 2020/0184729 A1* | 6/2020 | Jones ..................... G06F 3/011 |
| 2020/0188026 A1* | 6/2020 | de Souza ............. A61B 6/5223 |
| 2021/0361358 A1* | 11/2021 | May ........................ A61F 2/461 |

OTHER PUBLICATIONS

International Search Report and Written Opinion in corresponding International Application No. PCT/US2021/022887 mailed on Jun. 24, 2021, 6 pages.

* cited by examiner

AUGMENTED REALITY BASED SURGICAL NAVIGATION SYSTEM

CROSS-REFERENCE TO RELATED APPLICATIONS

This application is a national stage entry from International Application No. PCT/US2021/022887, filed on Mar. 18, 2021, published as International Publication No. WO 2021/188757 A1 on Sep. 23, 2021, and claims the benefit of U.S. Provisional Patent Application No. 62/992,655 filed on Mar. 20, 2020, the disclosures of which are hereby incorporated by reference in their entirety.

FIELD

This disclosure relates generally to surgical navigation systems, and in particular, to an augmented reality-based surgical navigation system.

BACKGROUND

Augmented Reality (AR) is a technology that superimposes or overlays a computer generated or virtual image on a user's view of the real world, thus providing a composite view of real world and virtual imagery. An AR headset or goggles may be used in conjunction with AR technology whereby virtual images may be displayed within the AR headset.

In various surgical procedures, devices, such as catheters, may need to be precisely inserted into the patient. Surgeons typically may rely on their general knowledge of anatomy and relatively crude and uncertain measurements for locating internal anatomical targets. One example is for a ventriculostomy surgical procedure, in which the surgeon must insert a catheter into the ventricle to drain cerebrospinal fluid (CSF). In this procedure, surgeons make measurements relative to cranial features to determine where to drill into the skull and then attempt to insert a catheter as perpendicular to the skull as possible.

Although ventriculostomy is one of the most commonly performed neurosurgical procedures, studies have shown a large number of misplaced catheters and many cases in which multiple attempts (passes) were required to hit the target (e.g., ventricle). Misplacement of the catheter can cause hemorrhage, infection and other injuries to the patient. These risks may be higher when the procedure is performed by a less experienced surgeon, which may occur in emergency situations.

SUMMARY

According to examples of the present disclosure, a computer-implemented method is disclosed that includes receiving, by an augmented reality device, a medical image of a surgical site, generating, by the augmented reality device, a virtual surgical site model based on the medical image; presenting, by the augmented reality device, the virtual surgical site model; receiving, by the augmented reality device, user calibration input; aligning, by the augmented reality device, the virtual surgical site model with a real-life surgical site based on the user calibration input; and displaying, by the augmented reality device and after the aligning, a virtual insertion path between an incision point and a target point to aid in inserting a tool as part of performing a surgical procedure.

Various additional features may be included in the computer-implemented method including one or more of the following features. The medical image comprises a segmented medical image and the virtual surgical site model identifies features from the segmented medical image. The computer-implemented method can further comprise determining a location of the target point based on the segmented virtual image. The computer-implemented method further comprises tracking of the tool such that a virtual extension of the tool is displayed by the augmented reality device. The medical image comprises one or more fiducials or features; the virtual surgical site model includes a representation of the one or more fiducials or features; the real-life surgical sites includes one or more fiducials features; and the aligning comprises aligning the respective locations of the one or more fiducials or features from the real-life surgical site with respective locations of the one or more fiducials or features on the virtual surgical site model. The user calibration input includes input identifying respective locations of the one or more fiducials or features on the real-life surgical site. The surgical navigation application automatically identifies the locations of the one or more fiducials or features on the real-life surgical site. The computer-implemented method further comprises receiving user input identifying an incision point, the virtual path being based on the user input identifying the incision point and the target point. The user calibration input is received via a trackable object. The surgical procedure comprises a ventriculostomy and the tool comprises a catheter.

According to examples of the present disclosure, a computer program product is disclosed that comprises a computer readable storage medium having program instructions embodied therewith, the program instructions executable by a computing device to cause the computing device to perform a method comprising: receiving, by an augmented reality device, a medical image of a surgical site, generating, by the augmented reality device, a virtual surgical site model based on the medical image; presenting, by the augmented reality device, the virtual surgical site model; receiving, by the augmented reality device, user calibration input; aligning, by the augmented reality device, the virtual surgical site model with a real-life surgical site based on the user calibration input; and displaying, by the augmented reality device and after the aligning, a virtual insertion path between an incision point and a target point to aid in inserting a tool as part of performing a surgical procedure.

Various additional features may be included in the computer program product including one or more of the following features. The medical image comprises a segmented medical image and the virtual surgical site model identifies features from the segmented medical image. The method can further comprise determining a location of the target point based on the segmented virtual image. The computer-implemented method further comprises tracking of the tool such that a virtual extension of the tool is displayed by the augmented reality device. The medical image comprises one or more fiducials or features; the virtual surgical site model includes a representation of the one or more fiducials or features; the real-life surgical sites includes one or more fiducials features; and the aligning comprises aligning the respective locations of the one or more fiducials or features from the real-life surgical site with respective locations of the one or more fiducials or features on the virtual surgical site model. The user calibration input includes input identifying respective locations of the one or more fiducials or features on the real-life surgical site. The surgical navigation application automatically identifies the locations of the one or more fiducials or features on the real-life surgical site. The method further comprises receiving user input identifying an incision point, the virtual path being based on the user input identifying the incision point and the target point. The user calibration input is received via a trackable object. The surgical procedure comprises a ventriculostomy and the tool comprises a catheter.

According to examples of the present disclosure, a system is disclosed that comprises a processor, a computer readable memory, a non-transitory computer readable storage medium associated with a computing device, and program instructions executable by the computing device to cause the computing device to perform a method comprising: receiving, by an augmented reality device, a medical image of a surgical site, generating, by the augmented reality device, a virtual surgical site model based on the medical image; presenting, by the augmented reality device, the virtual surgical site model; receiving, by the augmented reality device, user calibration input; aligning, by the augmented reality device, the virtual surgical site model with a real-life surgical site based on the user calibration input; and displaying, by the augmented reality device and after the aligning, a virtual insertion path between an incision point and a target point to aid in inserting a tool as part of performing a surgical procedure.

Various additional features may be included in the system including one or more of the following features. The medical image comprises a segmented medical image and the virtual surgical site model identifies features from the segmented medical image. The method can further comprise determining a location of the target point based on the segmented virtual image. The computer-implemented method further comprises tracking of the tool such that a virtual extension of the tool is displayed by the augmented reality device. The medical image comprises one or more fiducials or features; the virtual surgical site model includes a representation of the one or more fiducials or features; the real-life surgical sites includes one or more fiducials features; and the aligning comprises aligning the respective locations of the one or more fiducials or features from the real-life surgical site with respective locations of the one or more fiducials or features on the virtual surgical site model. The user calibration input includes input identifying respective locations of the one or more fiducials or features on the real-life surgical site. The surgical navigation application automatically identifies the locations of the one or more fiducials or features on the real-life surgical site. The method further comprises receiving user input identifying an incision point, the virtual path being based on the user input identifying the incision point and the target point. The user calibration input is received via a trackable object. The surgical procedure comprises a ventriculostomy and the tool comprises a catheter.

DETAILED DESCRIPTION

Figure 1A:
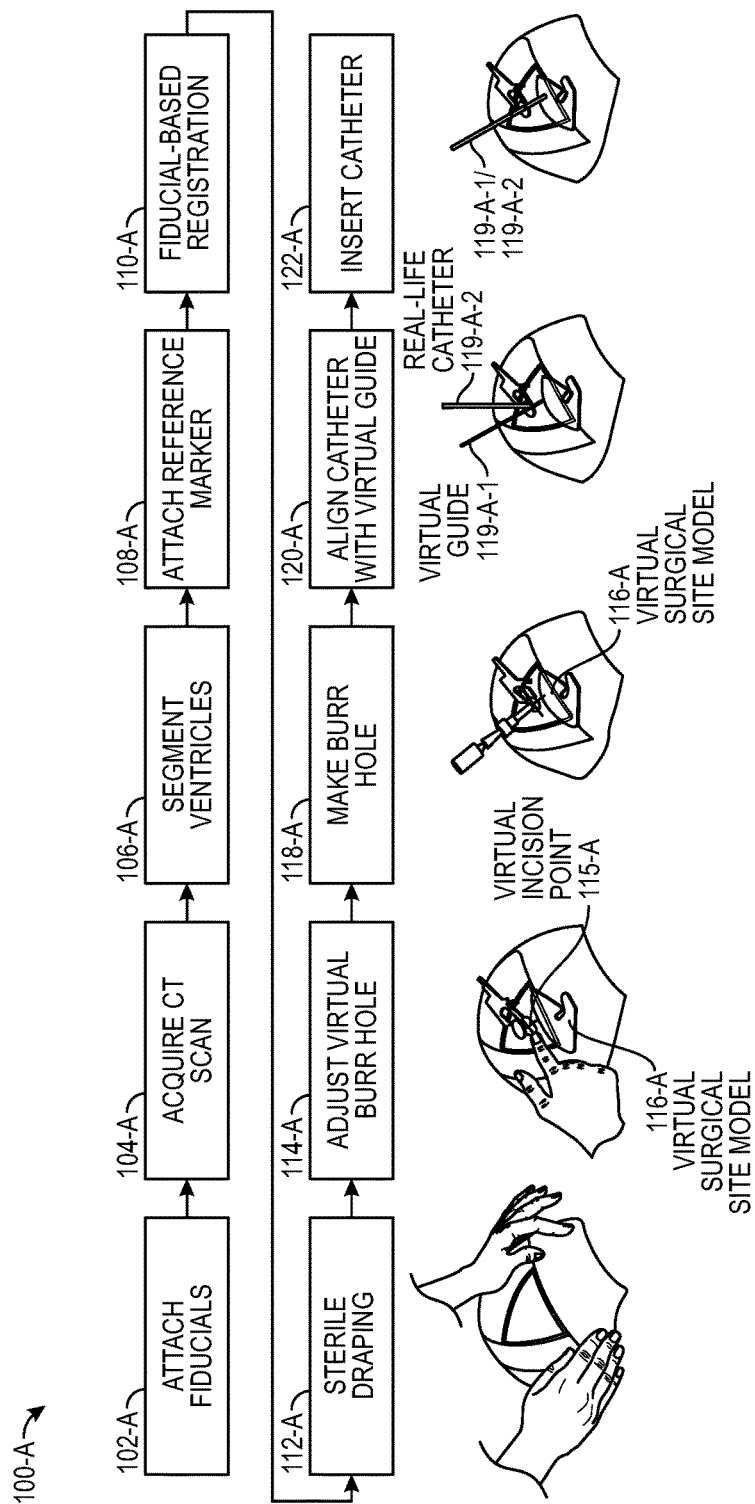
FIG. 1A and FIG. 1B illustrate overviews of example processes for providing guidance for placement of a catheter during a surgical procedure in accordance with aspects of the present disclosure.

Certain embodiments of the disclosure will hereafter be described with reference to the accompanying drawings, wherein like reference numerals denote like elements. It should be understood, however, that the accompanying drawings illustrate only the various implementations described herein and are not meant to limit the scope of various technologies described herein. The drawings show and describe various embodiments of the current disclosure.

In various surgical procedures, medical tools or devices such as catheters may need to be precisely inserted into the patient to minimize the risk of medical complications (e.g., infections, hemorrhages, etc.). The placement of these devices may be inaccurate, especially when the surgical procedure is being performed by a less experienced surgeon or doctor. Accordingly, aspects of the present disclosure may include a system and/or method to provide surgical procedure navigation via an augmented reality (AR) headset. In some embodiments, the surgical procedure navigation may aid in the insertion of a device for any variety of surgical procedures (e.g., a catheter in ventriculostomy). Further, as the systems and/or methods, described herein, may be implemented in an AR headset, the navigation and guidance techniques of the disclosure may be portable and may be used in a variety of settings (e.g., without the need of an elaborate operating room).

As described herein, aspects of the present disclosure may include a surgical navigation application hosted by an AR headset. In some embodiments, a surgeon may wear the AR headset during a surgical procedure and the AR headset, via the surgical navigation application may present a virtual path that guides the insertion of a device. As one illustrative example, the AR headset may present a virtual path that guides the insertion of a catheter as part of a ventriculostomy such that the catheter is inserted at the correct position (e.g., angle) so as to reach the target (e.g., the Foramen of Monro of the ventricles, or other target). As described herein, the surgical navigation application is not limited to providing navigation of catheter insertion for only a ventriculostomy, but may be used to aid catheter insertion (or insertion of other tools or devices) for other types of procedures.

In some embodiments, the surgical navigation application may present (e.g., through a display of the AR headset) a virtual surgical site that represents a real-life surgical site (e.g., a patient's skull, in the case of a ventriculostomy). The surgical navigation application may present the virtual path (to aid in catheter insertion) such that, when the AR headset is worn by a user (e.g., a surgeon), the user may follow the virtual path when inserting the catheter. As described herein, the surgical navigation application may generate the virtual path based on an image (e.g., CT scan or other type of medical imaging) in which the image may be used to identify the target. In order for the virtual surgical site and the virtual path to be aligned properly and accurately with the real-life surgical site, the surgical navigation application may include a calibration and alignment function, which may also be called a registration function.

As part of the calibration and alignment, fiducials or other types of markers may be attached to the real-life surgical site. An image (e.g., CT scan or other type of medical imaging) may be taken while the fiducials are attached to the real-life surgical site. In some embodiments, the image may be segmented to aid in identifying a location of a target (e.g., a ventricle). Further, segmenting the image may be performed to identify any features at the surgical site relevant to a surgical procedure (e.g., location of a ventricle or location of other organs). In other cases, an image be taken without fiducials attached to the real-life surgical site, so that existing identifiable features on the real-life surgical site may be used instead of fiducials.

The AR headset, using the surgical navigation application, may receive the segmented image and, based on the segmented image, may generate a virtual surgical site model to represent the real-life surgical site (e.g., a skull, in the case of a ventriculostomy). The AR headset may present the virtual surgical site model such that the user (e.g., surgeon) may view the virtual surgical site model through the AR headset.

When the virtual surgical site model is initially presented, the virtual surgical site model may be misaligned with the real-life surgical site. Thus, the surgical navigation application may include a calibration and alignment function to align the virtual surgical site model with the real-life surgical site. As described herein, a reference marker (detectable by the AR headset) may be attached to the real-life surgical site. The user may provide input to the surgical navigation application (e.g., via an accessory device, such as a trackable object or trackable pen) identifying the location of the fiducials on the real-life surgical site and/or identifiable features on the real-life surgical site. The use of the reference marker may aid the AR headset in tracking the trackable pen relative to the real-life surgical site and thus, accurately identifying the location of the fiducials or identifiable features that are inputted by the user. In some embodiments, the user may place the trackable object on or over the location of a fiducial or feature, and may provide input indicating to the surgical navigation application that the trackable object is located at the location of the fiducial or feature. In some embodiments, the user input may be provided via any variety of techniques (e.g., voice input, keyboard/mouse input, etc.). In other embodiments, the surgical navigation application may automatically identify the fiducials or features. Further, segmenting the image may be performed to identify any features at the surgical site relevant to a surgical procedure (e.g., location of a ventricle or location of other organs). In other cases, an image may be taken without fiducials attached to the real-life surgical site, so that existing identifiable features on the real-life surgical site may be used instead of fiducials.

Once the surgical navigation application has received the fiducial or feature point locations for the real-life surgical site, the surgical navigation application may align the virtual surgical site model to the real-world surgical site based on the received fiducial or feature point locations and the fiducial or feature points included in segmented surgical site image. That is, the surgical navigation application may shift, rotate, and/or reposition the virtual surgical site model such that the fiducials or features from the virtual surgical site model align with the fiducials or features from the real-life surgical site.

Upon alignment of the virtual surgical site model align with the real-life surgical site, the surgical navigation application may receive user input of the incision point. The surgical navigation application may then generate a virtual path between the incision point and the target. As described herein, the virtual surgical site model may include the target, as the virtual surgical site model was derived from the segmented image in which the target was identified. The surgical navigation application may present the virtual path within the AR display such that the user may view the path and insert the tool along the virtual path. As such, the insertion angle and/or position of a catheter (or other type of surgical tool) may be improved, thereby improving the results and safety of the surgical operation.

While the systems and/or methods described herein are described in terms of providing navigational aid for surgical operations, the systems and/or methods are not so limited. Similar techniques described herein may be applied to other technical areas, such as repair, maintenance, or other types of fields for guiding the placement, insertion, or position of an object (e.g., tool).

Embodiments of the disclosure may include a system, a method, and/or a computer program product at any possible technical detail level of integration. The computer program product may include a computer readable storage medium (or media) having computer readable program instructions thereon for causing a processor to carry out aspects of the present disclosure.

Figure 1B:
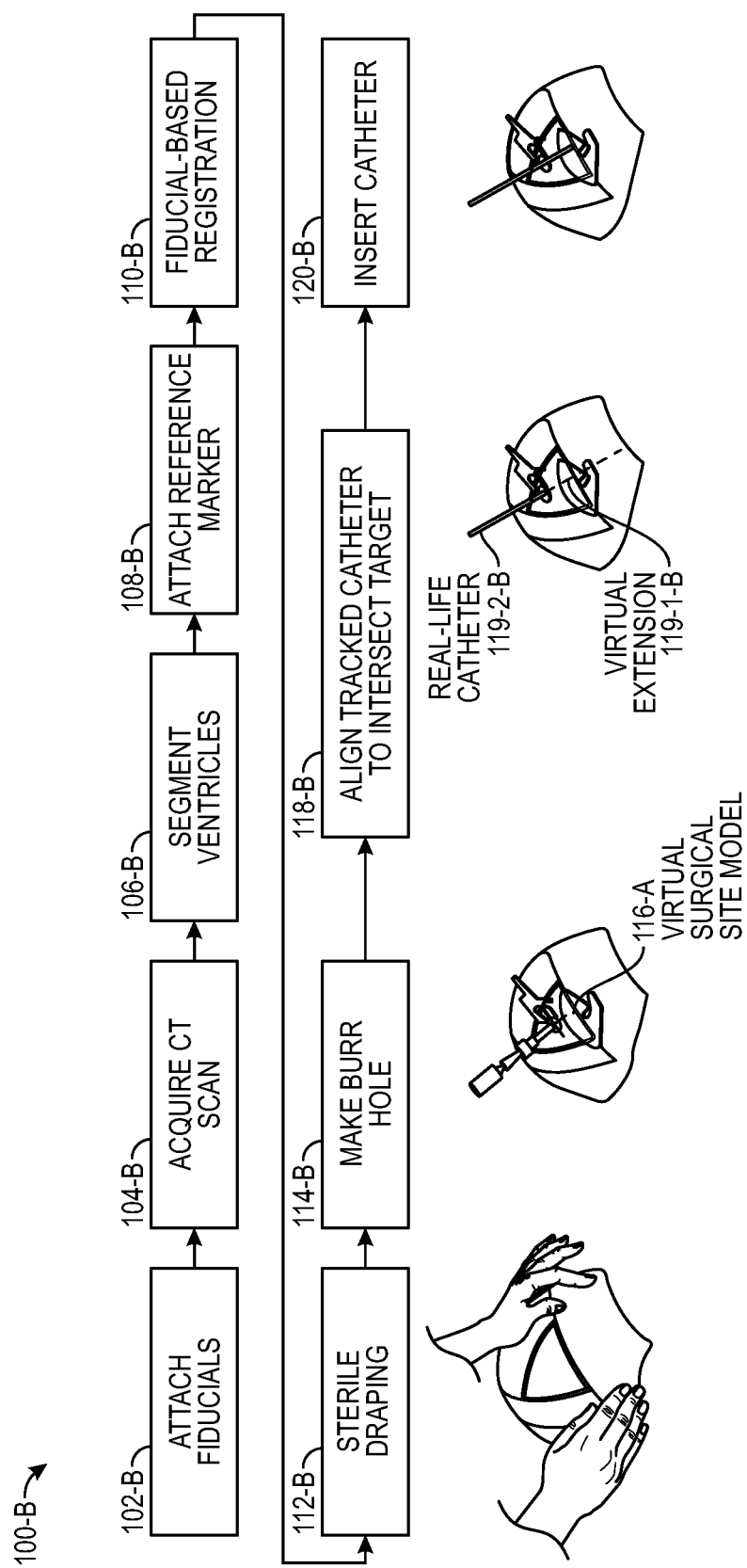

FIG. 1A and FIG. 1B illustrate overviews of example processes for providing guidance for placement of a medical tool during a surgical procedure in accordance with aspects of the present disclosure. More specifically, FIG. 1A illustrates an example process 100-A for providing guidance for placement of a medical tool (e.g., a catheter) during a ventriculostomy. As shown in FIG. 1A, at 102-A fiducials may be attached (e.g., to a surgical site, such as a patient's skull). At 104-A, an image scan (e.g., a CT scan) may be taken of the surgical site with the fiducials attached. At 106-A, the image may be segmented such that features relating to the surgical procedure may be identified. In the example of FIG. 1A, the ventricles may be segmented such that a target location (e.g., ventricle) may be identified from the segmented image. From the segmented image, a virtual surgical site model (e.g., virtual surgical site model 116-A) may be generated.

At 108-1A and 110-A, the virtual surgical site model may be calibrated to align the virtual surgical site model with the real-life surgical site. For example, at 108, a reference marker may be attached to the surgical site (e.g., the patient's skull). In some embodiments, the reference marker may include a marker that may be detected by an AR device (e.g., AR headset) and may be attached in a manner such that the marker is visible without covering the fiducials previously attached. At 110-A, fiducial-based registration is performed in which the surgical navigation application may automatically identify the fiducials (e.g., using computer vision) or in which a user (e.g., a surgeon), wearing the AR headset may provide user input to the surgical navigation application hosted by the AR headset, identifying the location of the fiducials on the real-life surgical site (e.g., via an accessory device, such as a trackable pen).

The use of the attached reference marker may aid the AR headset in tracking the trackable pen with respect to the real-life surgical site and thus, accurately identifying the location of the fiducials that are inputted by the user or are automatically detected. After the fiducial-based registration is completed (e.g., once the surgical navigation application has received the fiducial point locations for the real-life surgical site), the virtual surgical site model may be aligned with the real-life surgical site, and sterile draping may be performed to prepare the surgical site (at 112). At 114, the virtual surgical site model 116-A may be presented, including a virtual representation of a virtual incision point 115-A (e.g., burr hole). The surgical navigation application may receive user input to adjust or define the virtual incision point 115-A (e.g., the burr hole location).

At 118-A, the burr hole may be formed, and at 120-A, a virtual guide 119-A-1 may be presented. In some embodiments, the virtual guide 119-A-1 may be generated based on the location of the incision point, and the location of the target (e.g., ventricle) as determined from the segmented image represented in the virtual surgical site model 116-A. In some embodiments, the user (e.g., surgeon) may use the virtual surgical site model 116-A to accurately locate the target. Additionally, or alternatively, the surgical navigation application may identify the target based on, for example, pixel-based classification techniques and/or other image recognition techniques. The virtual guide 119-A-1 may be used to guide a real-life catheter 119-A-2. For example, at 122-A, the real-life catheter 119-A-2 may be aligned with the virtual guide 119-A-1. As a result of using the surgical navigation application and the AR headset, the catheter's placement position and angle may be improved.

FIG. 1B illustrates an example process for providing surgical navigation using a trackable medical tool (e.g., a trackable catheter). As shown in FIG. 1B, the process 100-B may include steps 102-B through 112-B, which may correspond to steps 102-A through 112-A of FIG. 1A. As further shown in FIG. 1B, the virtual surgical site model 116-B may be presented and a burr hole may be formed (at 114-B). In this embodiment, the virtual guide may include a virtual extension 119-1-B of the tracked real-life catheter 119-2-B. The virtual extension 119-1-B may include a line extending from the tip of the catheter along its axis. In this embodiment, the surgeon may not need to explicitly identify (e.g., to the surgical navigation application) the entry point or the target. In some embodiments, the virtual extension 119-1-B may move with the catheter so the user only needs to orient and insert the catheter such that the virtual extension continues to intersect the target. For example, at 118-B, and using the virtual extension 119-1-B, the tracked real-life catheter 119-2-B is aligned to intersect the target (e.g., as identified from the virtual surgical site model 116-B). At 120-B, the surgeon inserts the catheter while monitoring the location of the virtual extension 119-1-B, which is updated in real-time by the surgical navigation application based on tracking of the medical tool. For example, the surgeon may choose to realign the real-life catheter such that its virtual extension line continues to intersect the desired target point. Further, it is noted that while the virtual extension 119-1-B is shown as a line, in practice, the virtual extension 119-1-B may take a different form, such as a spiral, stack of concentric rings, or other type of visualization that helps the user to guide the medical tool (e.g., catheter) to the target.

Figure 2:
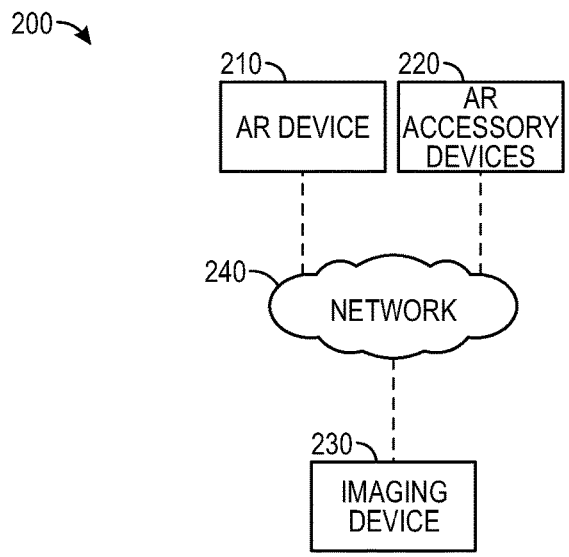
FIG. 2 illustrates an example environment in accordance with aspects of the present disclosure.

FIG. 2 illustrates an example environment in accordance with aspects of the present disclosure. As shown in FIG. 2, environment 200 includes an AR device 210, AR accessory devices 220, an imaging device 230, and a network 240. The AR device 210 may include any type of portable device, such as a virtual reality device, a head-mounted display, or the like. In some embodiments, the AR device 210 may host a surgical navigation application that may generate a virtual rendering of a surgical site, align the virtual surgical site with a real life surgical site based on a calibration process, determine a path between an incision point and a target, and present a virtual guide or virtual path between the incision point and the target. In some embodiments, the AR device 210 may communicate with one or more AR accessory devices 220 as part of the calibration process.

Further, the AR device 210 may communicate with the imaging device 230 to receive an image (e.g., a segmented image) of a surgical site in order for the AR device 210 to identify a target location and fiducials attached to the surgical site for aligning the virtual surgical model with the real-life surgical site.

The AR accessory devices 220 may include devices that may be used as part of a calibration processes for aligning a virtual surgical model (produced by the AR device 210) with a real-life surgical site. In some embodiments, the AR accessory devices 220 may include a trackable object (e.g., a trackable pen), a reference image, input devices, etc.

The imaging device 230 may include one or more computing devices that captures a medical image of a surgical site for a surgical procedure. In the example of a ventriculostomy, the surgical site may be a skull. The imaging device 230 may capture a medical image (e.g., a CT scan) while fiducials are attached such that a virtual surgical site model may be calibrated and aligned with a real-life surgical site.

The network 240 may include network nodes and one or more wired and/or wireless networks. For example, the network 240 may include a cellular network (e.g., a second generation (2G) network, a third generation (3G) network, a fourth generation (4G) network, a fifth generation (5G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network 240 may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks. In embodiments, the network 240 may include copper transmission cables, optical transmission fibers, wireless transmission, routers, firewalls, switches, gateway computers and/or edge servers.

The quantity of devices and/or networks in the environment 200 is not limited to what is shown in FIG. 2. In practice, the environment 200 may include additional devices and/or networks; fewer devices and/or networks; different devices and/or networks; or differently arranged devices and/or networks than illustrated in FIG. 2. Also, in some implementations, one or more of the devices of the environment 200 may perform one or more functions described as being performed by another one or more of the devices of the environment 200. Devices of the environment 200 may interconnect via wired connections, wireless connections, or a combination of wired and wireless connections.

Figure 3:
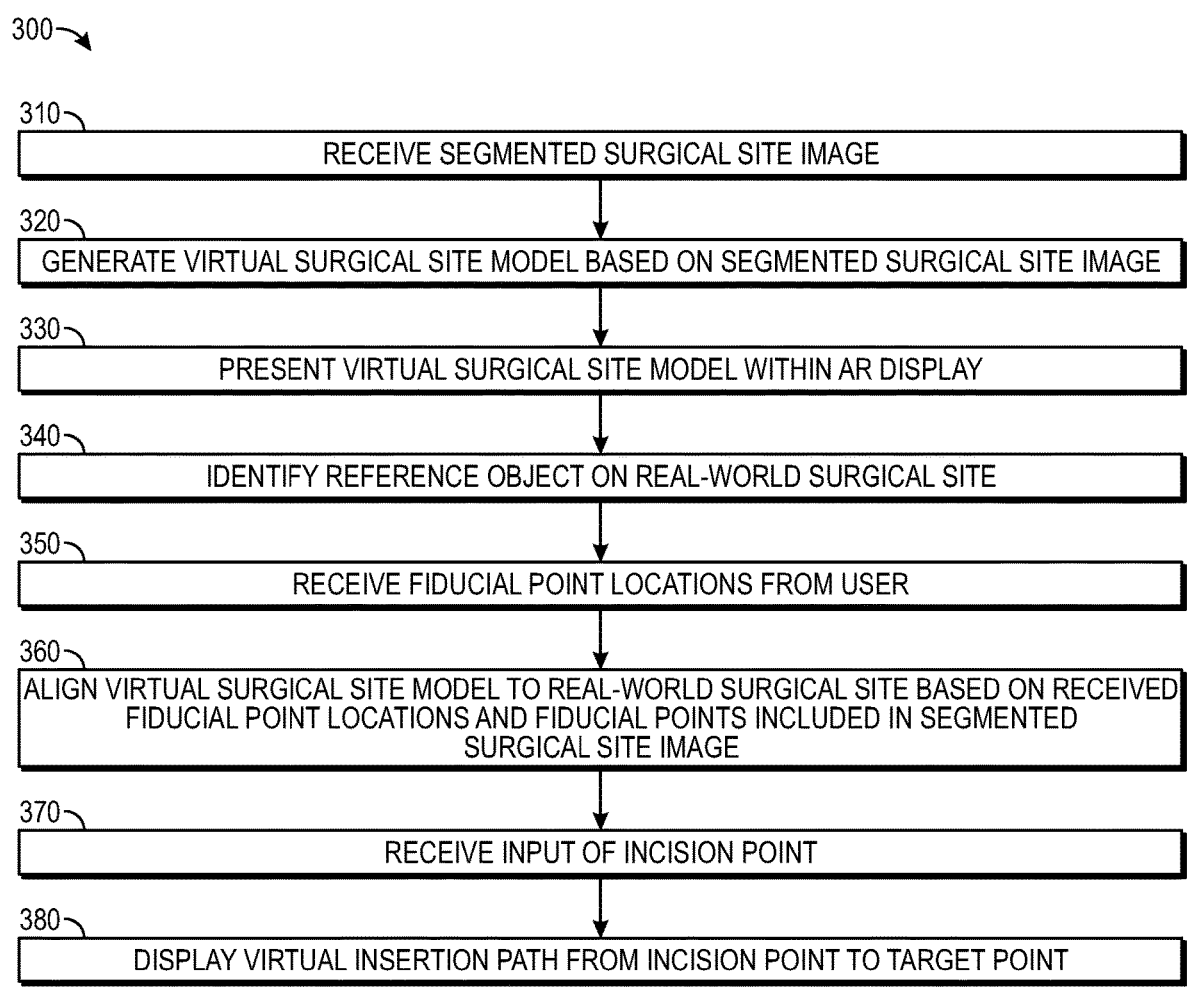
FIG. 3 illustrates an example flowchart of a process for generating and presenting a virtual insertion path to aid in the insertion of a surgical tool during a surgical procedure.

FIG. 3 illustrates an example flowchart of a process for generating and presenting a virtual insertion path to aid in the insertion of a surgical tool during a surgical procedure. The blocks of FIG. 3 may be implemented in the environment of FIG. 2, for example, and are described using reference numbers of elements depicted in FIG. 2. As noted herein, the flowchart illustrates the architecture, functionality, and operation of possible implementations of systems, methods, and computer program products according to various embodiments of the present disclosure. In some embodiments, the process of FIG. 3 may be performed by a surgical navigation application hosted on an AR device 210.

As shown in FIG. 3, process 300 may include receiving a segmented surgical site image (block 310). For example, the AR device 210 may receive a segmented surgical site image (e.g., from the imaging device 230). As described herein, the segmented surgical site image may include features at the surgical site relevant to a surgical procedure (e.g., location of a target, such as a ventricle or location of other organs). As described herein, the segmented image may show the fiducials attached to the surgical site.

Process 300 also may include generating a virtual surgical site model based on the segmented surgical site image (block 320). For example, the AR device 210 may generate a virtual surgical site model based on the segmented surgical site image. In some embodiments, the virtual surgical site model may include a segmented image of the real-life surgical site as well as the fiducials.

Process 300 further may include presenting the virtual surgical site model within the AR display (block 330). For example, the AR device 210 may present virtual surgical site model within the AR display. In this way, the user may view the virtual surgical site model through the display of the AR device 210. When the virtual surgical site model is initially presented, the virtual surgical site model may be misaligned with the real-life surgical site. Thus, the AR device 210 (e.g., through the surgical navigation application) may include a calibration and alignment function to align the virtual surgical site model with the real-life surgical site. Process blocks 340-360 may include process steps of the calibration and alignment function.

Figure 4A:
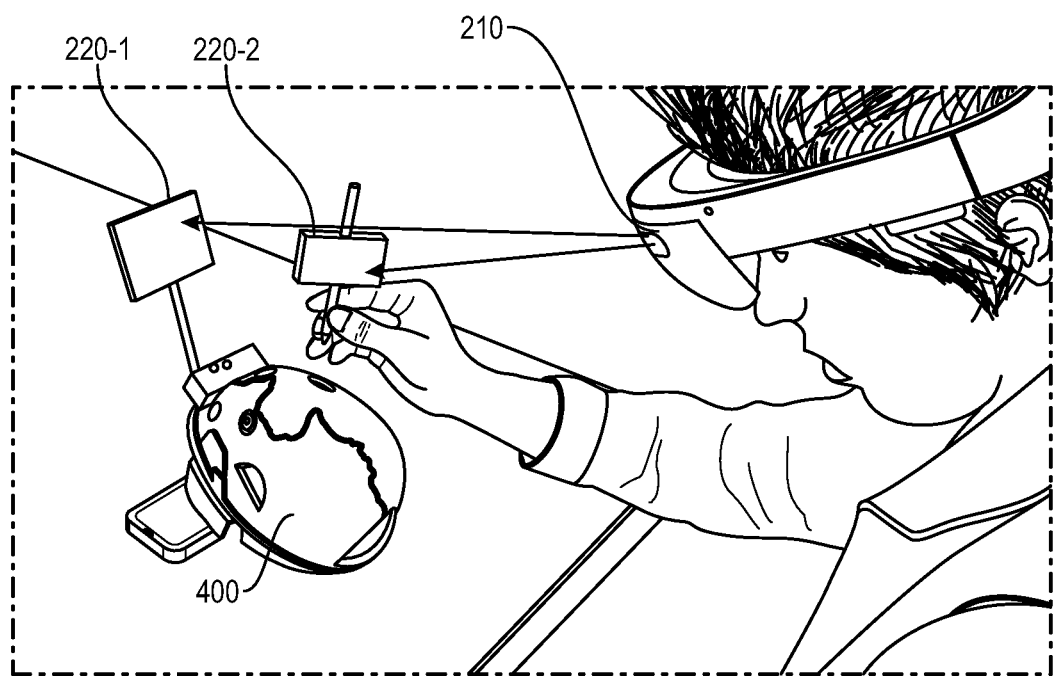
FIG. 4A, FIG. 4B, FIG. 4C, FIG. 4D, and FIG. 4E illustrate a calibration process and the presentation of a virtual insertion path as discussed in conjunction with the process of FIG. 3.

Process 300 also may include identifying a reference object on the real-world surgical site (block 340). For example, the AR device 210 may identify a reference object attached to a real-world surgical site (e.g., a patient's skull). As an example, referring to FIG. 4A, the reference object (e.g. accessory device 220-1) may be attached to a patient's skull (a replica of which is indicated by reference number 400). The reference object may be attached in a manner such that field of view of the AR device 210 includes the reference object as well as the trackable object (e.g., AR accessory device 220-2).

Figure 4B:
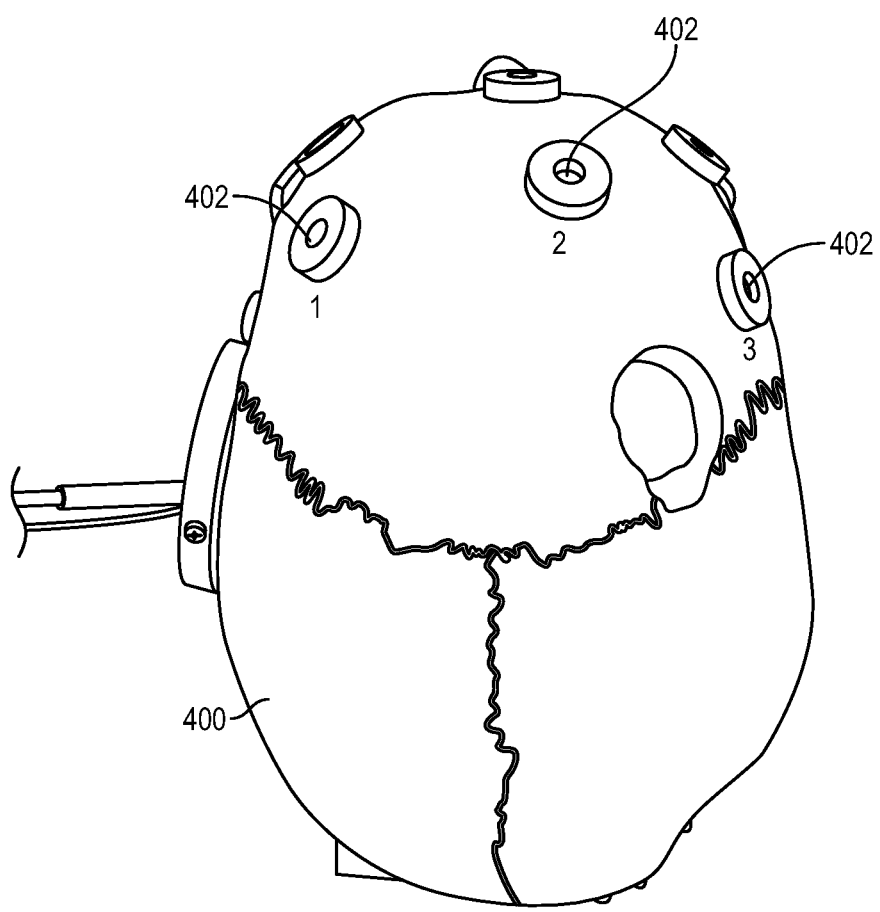

Process 300 further may include receiving fiducial point locations from the user (block 350). For example, the AR device 210 may receive fiducial point locations from the user using the trackable object in which the user places the trackable object at or above the fiducials of the real-life surgical site. An example of the fiducials 402 are shown in FIG. 4B.

Figure 4C:
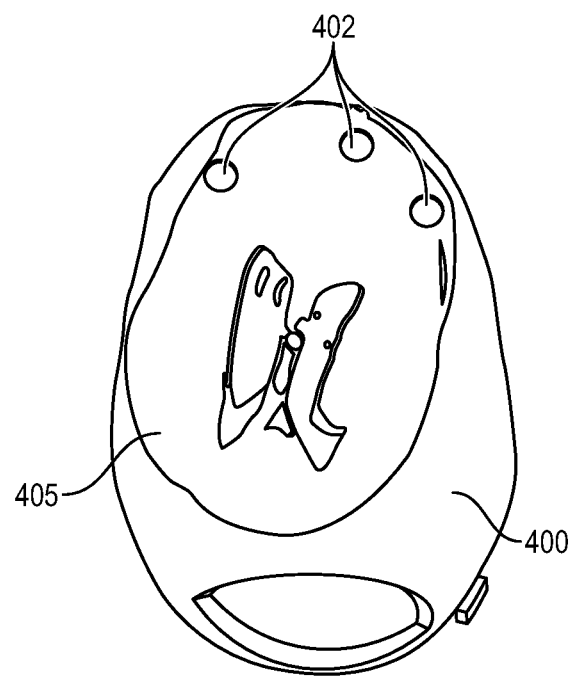

Referring to FIG. 4C, the AR device 210 may present a virtual surgical site model (e.g., a virtual skull 405). As shown in FIG. 4C, the virtual skull 405 may be initially misaligned with the real-life surgical site (e.g., skull replica 400). Thus, the user may provide user input identifying the locations of the fiducial points 402 on the real-life surgical site. In some embodiments, the user may place the trackable object on or over the location of a fiducial 402, and may provide input indicating to the surgical navigation application that the trackable object is located at the location of the fiducial. As described herein, the user input may be provided via any variety of techniques (e.g., voice input, keyboard/mouse input, etc.). In other embodiments, the surgical navigation application may automatically identify the locations of the fiducials, without user input. In yet other embodiments, existing features on the real-life surgical site (e.g., anatomic features) may be used instead of fiducials.

Process 300 also may include aligning the virtual surgical site model to the real world surgical site based on the received fiducial or feature point locations and the fiducial or feature points included in segmented surgical site image (block 360). For example, the AR device 210 may align the virtual surgical site model to the real-world surgical site.

Figure 4D:
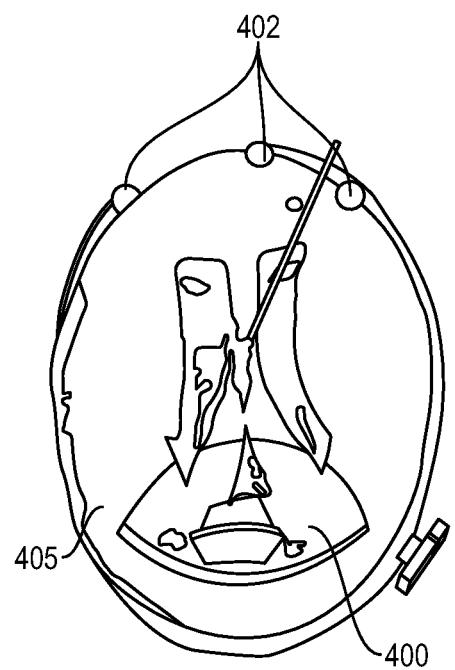

More specifically, the AR device 210 may shift, rotate, and/or reposition the virtual surgical site model such that the fiducials or features from the virtual surgical site model align with the fiducials or features from the real-life surgical site. Referring to FIG. 4D, the virtual surgical site model (e.g., the virtual skull 405) may be aligned with the real-life surgical site (e.g., the replica 400).

Process 300 further may include receiving input of the incision point (block 370). For example, the AR device 210 may receive user input identifying the incision point. In the case of a ventriculostomy, this may include a burr hole location.

Figure 4E:
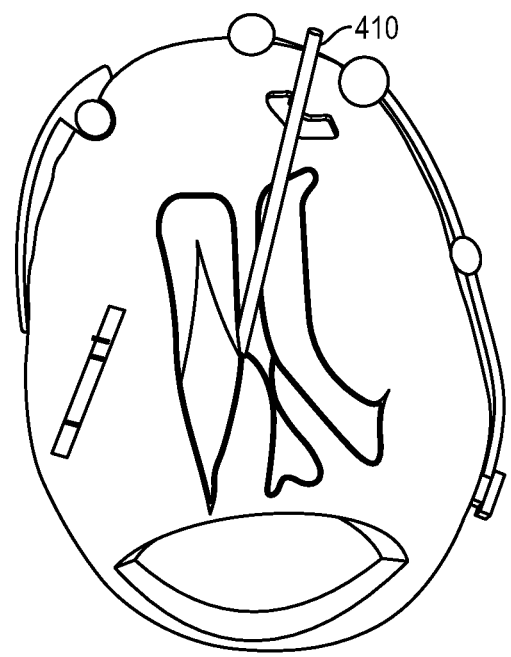

Process 300 further may include displaying a virtual insertion path from the incision point to a target point (block 370). For example, the AR device 210 may display a virtual insertion path from the incision point to the target point. In some embodiments, the target point may be determined based on the segmented surgical site image from which the virtual surgical site model is derived. Thus, the AR device 210 may determine the insertion path based on the incision point and the target, and may present the corresponding virtual insertion path. An example of the rendered virtual insertion path is shown in FIG. 4E (e.g., virtual insertion path 410). As further shown in FIG. 4E, the virtual surgical site model (e.g., the virtual skull) may identify features and/or other data from the segmented image. As a result of using the surgical navigation application and the AR headset 210 in accordance with the process 300 described herein, the catheter's placement position and angle may be improved, as the AR device 210 presents an accurate path from the incision point to the target. As such, any "guesswork" in locating the target and inserting a catheter in an effort to reach the target is eliminated.

FIG. 4A, FIG. 4B, FIG. 4C, FIG. 4D, and FIG. 4E illustrate a calibration process and the presentation of a virtual insertion path as discussed in conjunction with the process of FIG. 3 above.

Figure 5:
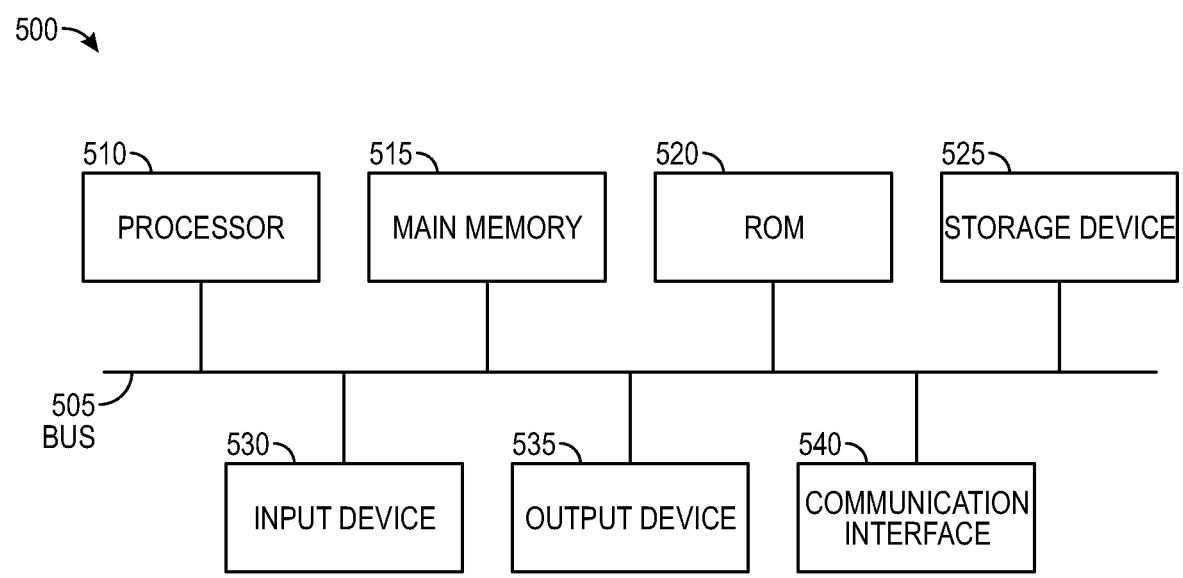
FIG. 5 illustrates example components of a device that may be used within environment of FIG. 2

FIG. 5 illustrates example components of a device 500 that may be used within environment 200 of FIG. 2. Device 500 may correspond to the AR device 210, the AR accessory devices 220, and/or the imaging device 230. Each of the AR device 210, the AR accessory devices 220, and/or the imaging device 230 may include one or more devices 500 and/or one or more components of device 500.

As shown in FIG. 5, device 500 may include a bus 505, a processor 510, a main memory 515, a read only memory (ROM) 520, a storage device 525, an input device 530, an output device 535, and a communication interface 540.

Bus 505 may include a path that permits communication among the components of device 500. Processor 510 may include a processor, a microprocessor, an application specific integrated circuit (ASIC), a field programmable gate array (FPGA), or another type of processor that interprets and executes instructions. Main memory 515 may include a random access memory (RAM) or another type of dynamic storage device that stores information or instructions for execution by processor 510. ROM 520 may include a ROM device or another type of static storage device that stores static information or instructions for use by processor 510. Storage device 525 may include a magnetic storage medium, such as a hard disk drive, or a removable memory, such as a flash memory.

Input device 530 may include a component that permits an operator to input information to device 500, such as a control button, a keyboard, a keypad, or another type of input device. Output device 535 may include a component that outputs information to the operator, such as a light emitting diode (LED), a display, or another type of output device. Communication interface 540 may include any transceiver-like component that enables device 500 to communicate with other devices or networks. In some implementations, communication interface 540 may include a wireless interface, a wired interface, or a combination of a wireless interface and a wired interface. In embodiments, communication interface 540 may receiver computer readable program instructions from a network and may forward the computer readable program instructions for storage in a computer readable storage medium (e.g., storage device 525).

Device 500 may perform certain operations, as described in detail below. Device 500 may perform these operations in response to processor 510 executing software instructions contained in a computer-readable medium, such as main memory 515. A computer-readable medium may be defined as a non-transitory memory device and is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. A memory device may include memory space within a single physical storage device or memory space spread across multiple physical storage devices.

The software instructions may be read into main memory 515 from another computer-readable medium, such as storage device 525, or from another device via communication interface 540. The software instructions contained in main memory 515 may direct processor 510 to perform processes that will be described in greater detail herein. Alternatively, hardwired circuitry may be used in place of or in combination with software instructions to implement processes described herein. Thus, implementations described herein are not limited to any specific combination of hardware circuitry and software.

In some implementations, device 500 may include additional components, fewer components, different components, or differently arranged components than are shown in FIG. 5.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the disclosure may include a system, a method, and/or a computer program product at any possible technical detail level of integration. The computer program product may include a computer readable storage medium (or media) having computer readable program instructions thereon for causing a processor to carry out or execute aspects and/or processes of the present disclosure.

In embodiments, the computer readable program instructions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on a user's computer, partly on the user's computer, as a stand-alone software package, partly on the user's computer and partly on a remote computer or entirely on the remote computer or server.

In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

In embodiments, a service provider could offer to perform the processes described herein. In this case, the service provider can create, maintain, deploy, support, etc., the computer infrastructure that performs the process steps of the disclosure for one or more customers. These customers may be, for example, any business that uses technology. In return, the service provider can receive payment from the customer(s) under a subscription and/or fee agreement and/ or the service provider can receive payment from the sale of advertising content to one or more third parties.

The foregoing description provides illustration and description, but is not intended to be exhaustive or to limit the possible implementations to the precise form disclosed. Modifications and variations are possible in light of the above disclosure or may be acquired from practice of the implementations.

It will be apparent that different examples of the description provided above may be implemented in many different forms of software, firmware, and hardware in the implementations illustrated in the figures. The actual software code or specialized control hardware used to implement these examples is not limiting of the implementations. Thus, the operation and behavior of these examples were described without reference to the specific software code—it being understood that software and control hardware can be designed to implement these examples based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

While the present disclosure has been disclosed with respect to a limited number of embodiments, those skilled in the art, having the benefit of this disclosure, will appreciate numerous modifications and variations there from. It is intended that the appended claims cover such modifications and variations as fall within the true spirit and scope of the disclosure.

No element, act, or instruction used in the present application and the attached appendix should be construed as critical or essential unless explicitly described as such. It is further emphasized that the attached appendix is provided for illustrative purposes only and is not meant to limit the systems and/or methods described herein. Also, as used herein, the article "a" is intended to include one or more items and may be used interchangeably with "one or more." Where only one item is intended, the term "one" or similar language is used. Further, the phrase "based on" is intended to mean "based, at least in part, on" unless explicitly stated otherwise.

What is claimed is:

1. A computer-implemented method comprising:
   receiving, by an augmented reality device, a medical image of a surgical site,
   generating, by the augmented reality device, a virtual surgical site model based on the medical image;
   presenting, by the augmented reality device, the virtual surgical site model;
   receiving, by the augmented reality device, user calibration input;
   aligning, by the augmented reality device, the virtual surgical site model with a real-life surgical site based on the user calibration input; and
   displaying, by the augmented reality device and after the aligning, a virtual insertion path between an incision point and a target point to aid in inserting a tool as part of performing a surgical procedure.

2. The method of claim 1, wherein the medical image comprises a segmented medical image and the virtual surgical site model identifies features from the segmented medical image.

3. The method of claim 2, further comprising determining a location of the target point based on the segmented virtual image.

4. The method of claim 2, further comprising tracking of the tool such that a virtual extension of the tool is displayed by the augmented reality device.

5. The method of claim 1, wherein:
   the medical image comprises one or more fiducials or features;
   the virtual surgical site model includes a representation of the one or more fiducials or features;
   the real-life surgical site includes one or more fiducials or features; and
   the aligning comprises aligning the respective locations of the one or more fiducials or features from the real-life surgical site with respective locations of the one or more fiducials or features on the virtual surgical site model.

6. The method of claim 5, wherein the user calibration input includes input identifying respective locations of the one or more fiducials or features on the real-life surgical site.

7. The method of claim 5, where the surgical navigation application automatically identifies the locations of the one or more fiducials or features on the real-life surgical site.

8. The method of claim 1, further comprising receiving user input identifying an incision point, the virtual path being based on the user input identifying the incision point and the target point.

9. The method of claim 1, wherein the user calibration input is received via a trackable object.

10. The method of claim 1, wherein the surgical procedure comprises a ventriculostomy and the tool comprises a catheter.

11. A computer program product comprising a computer readable storage medium having program instructions embodied therewith, the program instructions executable by a computing device to cause the computing device to perform a method comprising:
    receiving, by an augmented reality device, a medical image of a surgical site,
    generating, by the augmented reality device, a virtual surgical site model based on the medical image;
    presenting, by the augmented reality device, the virtual surgical site model;
    receiving, by the augmented reality device, user calibration input;
    aligning, by the augmented reality device, the virtual surgical site model with a real-life surgical site based on the user calibration input; and
    displaying, by the augmented reality device and after the aligning, a virtual insertion path between an incision point and a target point to aid in inserting a tool as part of performing a surgical procedure.

12. The computer program product of claim 11, wherein the medical image comprises a segmented medical image and the virtual surgical site model identifies features from the segmented medical image.

13. The computer program product of claim 12, wherein the method further comprises determining a location of the target point based on the segmented virtual image.

14. The computer program product of claim 12, wherein the method further comprises tracking of the tool such that a virtual extension of the tool is displayed by the augmented reality device.

15. The computer program product of claim 11, wherein:
the medical image comprises one or more fiducials or features;
the virtual surgical site model includes a representation of the one or more fiducials or features;
the real-life surgical site includes one or more fiducials or features; and
the aligning comprises aligning the respective locations of the one or more fiducials or features from the real-life surgical site with respective locations of the one or more fiducials or features on the virtual surgical site model.

16. The computer program product of claim 15, wherein the user calibration input includes input identifying respective locations of the one or more fiducials or features on the real-life surgical site.

17. The computer program product of claim 15, where the surgical navigation application automatically identifies the locations of the one or more fiducials or features on the real-life surgical site.

18. The computer program product of claim 11, wherein the method further comprises receiving user input identifying an incision point, the virtual path being based on the user input identifying the incision point and the target point.

19. The computer program product of claim 11, wherein the user calibration input is received via a trackable object.

20. A system comprising:
a processor, a computer readable memory,
a non-transitory computer readable storage medium associated with a computing device, and program instructions executable by the computing device to cause the computing device to perform a method comprising:
receiving, by an augmented reality device, a medical image of a surgical site,
generating, by the augmented reality device, a virtual surgical site model based on the medical image;
presenting, by the augmented reality device, the virtual surgical site model;
receiving, by the augmented reality device, user calibration input;
aligning, by the augmented reality device, the virtual surgical site model with a real-life surgical site based on the user calibration input; and
displaying, by the augmented reality device and after the aligning, a virtual insertion path between an incision point and a target point to aid in inserting a tool as part of performing a surgical procedure.

* * * * *